United States Patent [19]

Quesenberry et al.

[11] Patent Number: 5,264,418

[45] Date of Patent: Nov. 23, 1993

[54] HEMOLYMPHOPOIETIC GROWTH FACTORS, PROCESS FOR PURIFYING AND PRODUCING HEMOLYMPHOPOIETIC GROWTH FACTORS AND PHARMACEUTICAL COMPOSITIONS MADE THEREFROM

[75] Inventors: Peter J. Quesenberry; Ian K. McNiece, both of Charlottesville, Va.

[73] Assignee: The University of Virginia Alumni Patents Foundation, Charlottesville, Va.

[21] Appl. No.: 128,266

[22] Filed: Dec. 3, 1987

Related U.S. Application Data

[63] Continuation-in-part of Ser. No. 822,170, Jan. 24, 1986, abandoned.

[51] Int. Cl.$^5$ .............. C07K 3/20; C07K 15/06; A61K 37/02
[52] U.S. Cl. .............................. 514/12; 514/2; 514/21; 530/399; 530/413; 530/412; 530/838; 435/172.3; 435/240.2
[58] Field of Search .............. 530/324, 399, 412, 413, 530/838; 514/2, 12, 21

[56] References Cited

U.S. PATENT DOCUMENTS 4,868,119 9/1989 Clark .............................. 435/172.3

OTHER PUBLICATIONS

Song et al., "Functional and Morphologic Characterization of a Cell Line Derived from Adherent Mouse Stromal Cells", Exp. Hematol, p. 106 (USA 1983).
Song et al., "Long-Term Hemopoiesis Supported by a Subclone Isolated from Murine Bone Marrow Stromal Cell Line TC-1", Exp. Hematol, p. 463 (USA 1984).
Mori et al., "Stimulation and Support of Haemopoietic Stem Cell Proliferation . . . ", J. Radiat, pp. 109-115 (USA 1981).
Friedenstein et al., "Stromal Cells Responsible for Transferring the Microenvironment of the Hemopoietic Tissues", Transplantation, pp. 331-340 (USA 1974).
Westen et al., "Association of Alkaline-Phosphatase-Positive Reticulum Cells in Bone Marrow . . . ", J. Exp. Med., pp. 919-937 (USA 1979).
Quesenberry et al., "Studies of the Control of Hemopoiesis in Dexter Cultures", Long-Term Bone Marrow Culture, pp. 171-193 (USA 1984).
Schofield, "The Relationship Between the Spleen Colony-Forming Cell and the Heemopoietic Stem Cell", Blood Cells, pp. 7-25 (USA 1978).
Toksoz et al., "The Regulation of Hemopoiesis in Long-Term Bone Marrow Cultures . . . ", Blood, pp. 931-936 (USA 1980).
Lanotte et al., "Histochemical and Ultrastructural Characteristics of a Cell Line . . . ", J. Cell Science, pp. 281-297 (Great Britain 1981).
Song et al., "Hemopoietic Factor Production by TC-1, A Dexter Derived Murine Marrow Adherent Cell Line", Blood, p. 141a (USA 1983).
Quesenberry et al., *Blood*, 65, Nal, 214-217, 1985.

*Primary Examiner*—F. T. Moezie
*Attorney, Agent, or Firm*—James Creighton Wray

[57] ABSTRACT

This invention relates to hemolymphopoeitic growth factors (HLGF-1) that synergize with CSF-1, IL3 and GM-CSF and have pre-B cell potentiating activity. The invention also relates to a process for purifying such HLGF-1's from murine marrow cells and for producing such HLGF-1s by hosts transformed with recombinant DNA molecules comprising DNA sequences encoding the growth factor, and to methods of treatment and compositions characterized by HLGF-1s. These methods and agents are useful in immunoregulatory and hemopoietic applications and therapies.

5 Claims, 3 Drawing Sheets

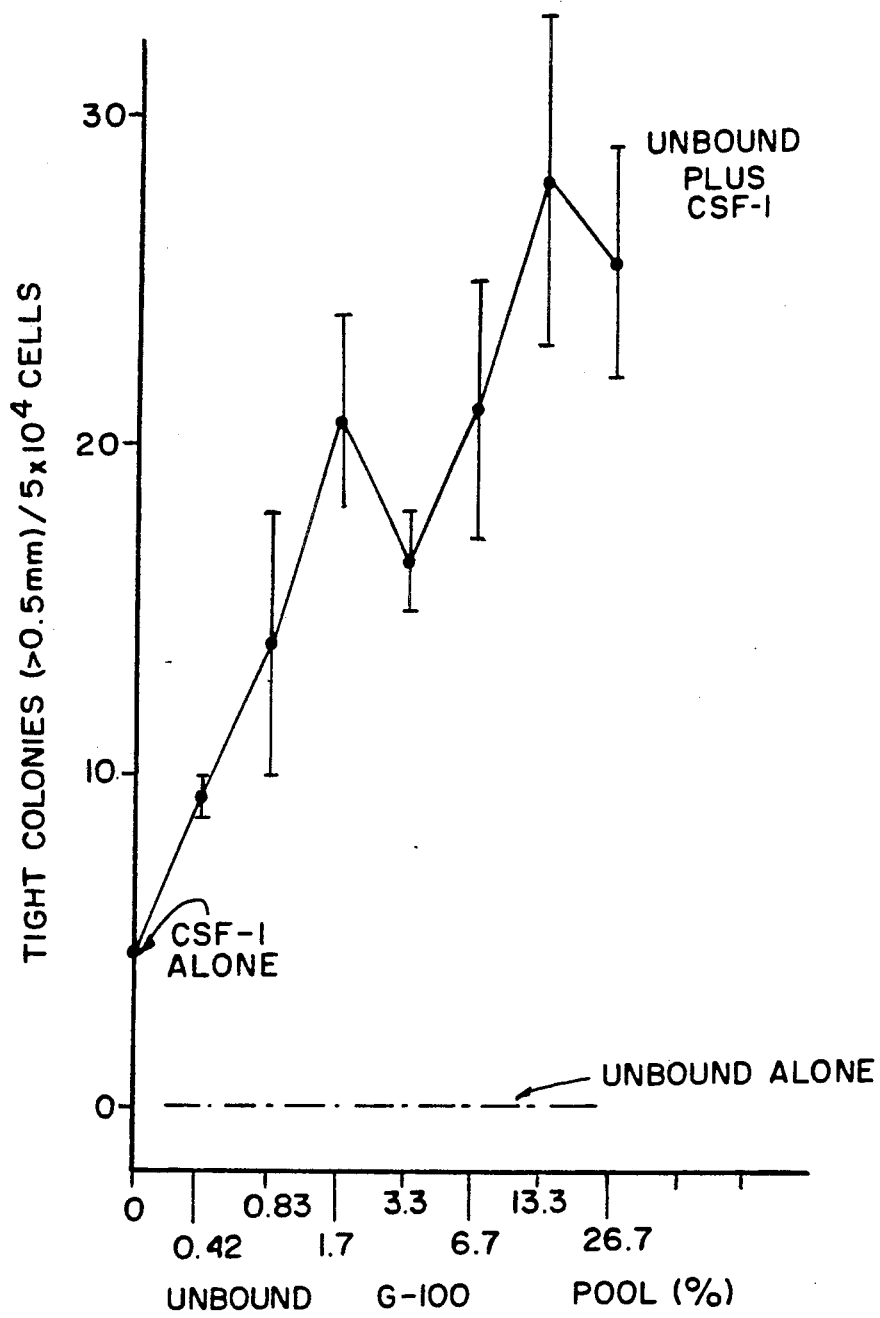
FIG. I

FIG. 2b
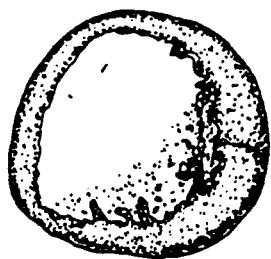
FIG. 2a
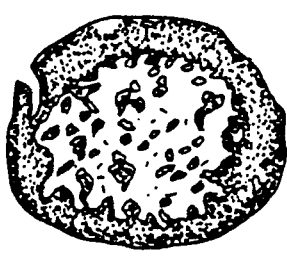
FIG. 2c
FIG. 3b
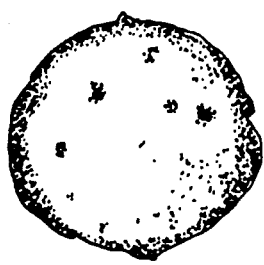
FIG. 3a
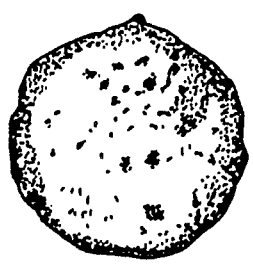
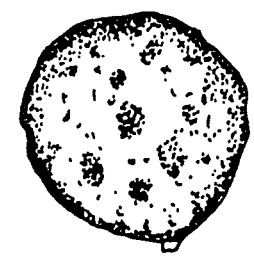
FIG. 3c

HEMOLYMPHOPOIETIC GROWTH FACTORS, PROCESS FOR PURIFYING AND PRODUCING HEMOLYMPHOPOIETIC GROWTH FACTORS AND PHARMACEUTICAL COMPOSITIONS MADE THEREFROM

This is a continuation-in-part of U.S. Ser. No. 822,170, filed Jan. 24, 1986, now abandoned.

TECHNICAL FIELD OF THE INVENTION

This invention relates to hemolymphopoeitic growth factors (HLGF-1) that synergize with CSF-1, IL3 and GM-CSF and have pre-B cell potentiating activity. The invention also relates to a process for purifying such HLGF-1's from murine marrow cells and for producing such HLGF-1s by hosts transformed with recombinant DNA molecules comprising DNA sequences encoding the growth factor, and to methods of treatment and compositions characterized by HLGF-1s. These methods and agents are useful in immunoregulatory and hemopoietic applications and therapies.

BACKGROUND ART

Residing mostly in the bone marrow are pluripotent stem cells giving rise to various blood cells. Proliferation and differentiation of the blood cell progeny is regulated by a series of myleloid growth factors thought to be produced in stromal cells, also contained in the marrow microenvironment [N. S. Wolf, "The Hemopoietic Microenvironment", Hematol, 8, p. 469 (1979); D. Zipori, "Cultured Stromal Cell Lines From Hemopoietic Tissues". In: Blood Cell Formation ed. M. Tanassoli, Marcel Dekker, Inc. In Press]. These myleloid growth factors are labelled hematopoietic colony-stimulating factors, or CSF'S. Macrophage-CSF (M-CSF or CSF-1) stimulates the formation of monocytes/macrophages; granulocytemacrophage-CSF (GM-CSF) having a broad range of activity, stimulates the formation of neutrophils (or granulocytes), monocytes/macrophages, eosinophils, erythrocytes and megakaryocytes [P. H. Plusnik et al., *J. Cell. Comp. Physiol.*, 66, p. 319 (1965); D. Metcalf, "The Hemopoietic Colony Stimulating Factors" (Elsevier, Amsterdam, 1984)]; and, multi-CSF (Interleukin 3 or IL3) stimulates the formation of neutrophils, monocytes/macrophages, eosinophils, megakaryocytes as well as basophils [P. Quesenberry et al., "The Effect of IL3 and GM-CSA-2 On Megakaryocytes and Myeloid Clonal Colony Formation", *Blood*, 65, p. 214 (1985)].

As a result of their biological properties GM-CSF, CSF-1 and IL3, may be used for various types of therapy requiring stimulation of the differentiation or proliferation of various hematopoietic lineages. For example, therapy with the growth factors given prior to, concommitantly with, or following chemotherapy or radiation, to increase or maintain blood count would be useful for cancer and autoimmune diseases. Bacterial, fungal or other infections could thus be obviated in these patients having a reduced level of neutrophilic granulocytes from the chemotherapy or radiotherapy. More specifically, GM-CSF and IL3 could be used as an adjuvant during bone marrow transplants, both for cancer and noncancer treatment, for example, thalassemia. Furthermore, GM-CSF and IL-3 can act as differentiation agents, beneficial in the treatment of bone marrow cell differentiation disorders such as leukemia. Also, they may be useful in the treatment of congenital and acquired aplastic anemias in which there is a deficiency of activated bone marrow stem cells.

Also derived from pluripotent stem cells are antigen responsive B lymphocytes ("pre-B cells"), the precursors of plasma cells which are highly specialized for antibody production and secretion. Briefly, antigens react with B cell surface bound antibodies to produce plasma cells. Little is known about regulatory events for pre-B cell development or components of the marrow microenvironment which may mediate pre-B cell differentiation.

Because of the important therapeutic potential of the growth factors GM-CSF, CSF-1 and IL3, and the importance of regulating the production of B cells, it would therefore be of interest to identify and isolate a hemolymphopoietic growth factor (HLGF-1) which augments the effect of or synergizes with GM-CSF, CSF, CSF-1 and IL3, while also being capable of potentiating pre-B cell production.

At present, compounds reported as displaying synergy with CSF-1 in supporting the proliferation of monocytes/macrophages include IL3 and hemopoietin-1 [E. R. Stanley et al., "Factors affecting The Growth And Differentiation Of Hemopoietic Cells In Culture", *Clin. Haematal*, 13, p. 329 (1984); S. H. Bartelmez et al., "Synergism Between Hemopoietic Growth Factor Detected By Their Effects On Cells Bearing Receptors For A Lineage Specific HGF: Assay Of Hemopoietin-1", *J. Cell Physiol*, 122, p. 370 (1985); I. McNiese et al., "Recombinant Interleukin-3 Exhibits Synergistic Factor Activity", *Cell. Biol. Int. Rep.*, 8, p. 812 (1984)]. However, IL3 and hemopoietin-1 have not been demonstrated to also induce pre-B cell formation. Synergistic activity for giant macrophage colony formation has also been shown by combining pregnant uterus extract (as the colony stimulating factor) with human spleen-conditioned medium in nutrient agar cultures but without pre-B-inducing activity [T. R. Bradley, "Detection of Primitive Macrophage Progenitor Cells in Mouse Bone Marrow", *Blood*, 54, p. 1446 (1979)].

DISCLOSURE OF THE INVENTION

The present invention relates to a substantially pure hemolymphopoietic growth factor, HLGF-1, capable of synergizing with GM-CSF, CSF-1 and IL3 and exhibiting a pre-B cell inducing activity for use in immunoregulatory and hemopoietic compositions, methods and therapies. The HLGF-1 of the invention is also characterized by a molecular weight of approximately 110–140 kD.

One embodiment of a process of this invention for producing HLGF-1 is purification from natural sources. Such purification comprises the steps of 1) anion exchange chromatography on a DEAE zeta prep; 2) con-A affinity chromatography; 3) Sephacryl S-300 gel filtration chromatography; 4) anion exchange on a mono-Q column; and 5) Superose 12 column gel filtration chromatography.

A second embodiment of a process of this invention for producing HLGF-1 is the recombinant production of such growth factor. In such a process, DNA sequences that code for HLGF-1 of this invention, recombinant DNA molecules characterized by those sequences and various unicellular hosts transformed with those DNA sequences and molecules are employed to produce HLGF-1 of this invention by fermentation of the transformed hosts.

BRIEF DESCRIPTION OF THE DRAWINGS

FIG. 1 displays HLGF-1's capacity to synergize colony formation by CSF-1. TC-1 CM purified by DEAE cellulose, Sephadex G-100 chromatography and CSF-1 antibody affinity chromatography was cultured with CSF-1 and marrow cells from BDF1 mice in single-layer agar cultures. Results are expressed as colonies per $5 \times 10^4$ cells.

FIG. 2 displays HLGF-1's capacity to synergize giant colony formation by IL3. TC-1 CM was passed over a Sepharose column to deplete CSF-1 and then added to post-5-fluorouracil BDF1 marrow cells in a double-layer agar assay with a source of CSF-1.

FIG. 3 displays HLGF-1's capacity to synergize giant mixed granulocyte-macrophage colonies by GM-CSF. TC-1 CM was added to murine BDF1 marrow cells in a double-layer agar assay with a source of GM-CSF.

DETAILED DESCRIPTION OF THE INVENTION

Figure 4:
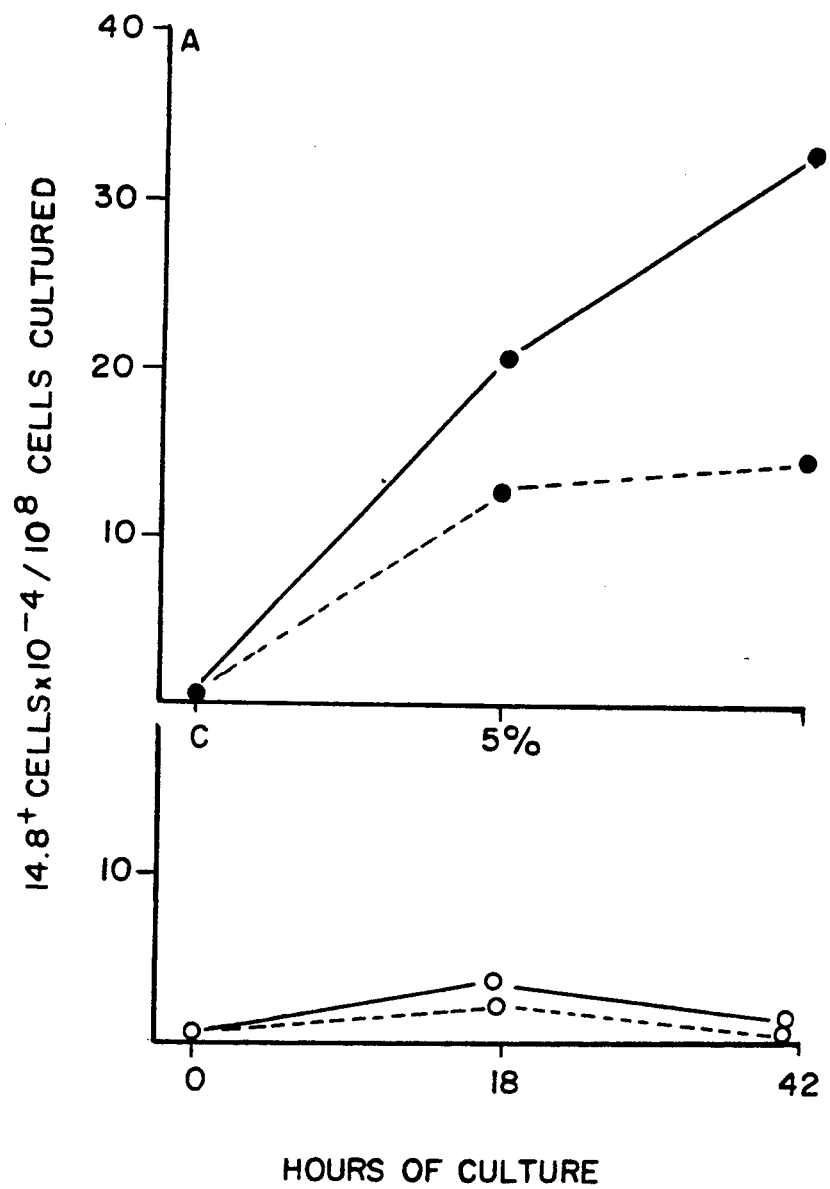
FIG. 4 displays increased levels of pre-B cell production upon the addition of 5% or 10% TC-1 CM to culture medium. Data is presented as absolute numbers of pre-B cells or 14.8+cells generated per $10^6$ cells cultured.

In order that the invention herein described may be fully understood, the following detailed description is set forth.

In the description, the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal.

Gene—A DNA sequence which encodes through its template or messenger RNA ("mRNA") a sequence of amino acids characteristic of a specific polypeptide.

Transcription—The process of producing mRNA from a gene.

Translation—The process of producing a polypeptide from mRNA.

Expression—The process undergone by a DNA sequence or gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet ®) transforms a cell previously sensitive to tetracycline into one which is resistant to it. A cell transformed by a plasmid is called a "transformant".

Phage or Bacteriphage—Bacterial virus many of which consist of DNA sequences encapsidated in a protein envelope or coat ("capsid").

Cloning Vehicle—A plasmid, phage DNA or other DNA sequence which is able to replicate in a host cell, which is characterized by one or a small number of endonuclease recognition sites at which such DNA sequence may be cut in a determinable fashion without attendant loss of an essential biological function of the DNA, e.g., replication, production of coat proteins or loss of promoter or binding sites, and which contains a marker suitable for us in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end and have the capacity to infect some host cell and be maintained therein.

Expression Control Sequence—A sequence of nucleotides that controls and regulates expression of genes when operatively linked to those genes. They include the lac system, the trp system, the tac system, the trc system, major operator and promoter regions of phage λ, the control region of fd coat proteins, the early and late promoters of SV40, promoters derived from polyoma, adenovirus and simian virus, the promoter for 3-phosphoglycerate kinase or other glycolytic enzymes, the promoters of yeast acid phosphotase, e.g., Pho 5, the promoters of the yeast -mating factors, and other sequences known to control the expression of genes of prokaryotic or eukaryotic cells and their viruses, or combinations thereof.

Hemolymphopoetic Growth Factor (HLGF-1)—A compound displaying synergistic activity with CSF-1, IL-3 and GM-CSF and having pre-B cell inducing activity.

As described above, HLGF-1 of this invention is capable of synergizing with CSF-1, IL3 and GM-CSF and inducing pre-B cell generation. Our assays utilized conditioned media from a TC-1 cell line derived from C57B1/6J murine marrow from which HLGF-1 is derived according to the process of the invention. Using giant macrophage colony formation of greater than 0.5-mm diameter dense colonies and clonal agar cultures with and without added pure CSF-1, the CSF-1-dependent synergistic activity present in TC-1-CM is characterized. TC-1 CM in this assay is separated by DE-52 cellulose chromatography followed by G100 Sephadex chromatography. Synergism with IL3 is determined using the formation of 1 mm and 2 mm megakaryocyte and giant granulocyte macrophage and granulocyte macrophate-megakaryocyte colonies in a single layer agar culture in the presence of TC-1 CM depleted of CSF-1 because CSF-1 is known to act synergistically with IL3. We further tested to see if the synergistic activity effected the stimulation of overall colony formation or just an increase in colony size. After culturing post-5-fluorouracil (5-FU) marrow cells in a double-layer agar assay with TC-1 CM previously passed through a Sepharose column plus IL3 we found the major effect of the synergistic activity is to increase colony size with no overall stimulation of total colony formation. Synergism with GM-CSF is determined using the formation of granulocyte macrophages and macrophage colonies in a single-layer agar culture in the presence of TC-1 CM depleted of CSF-1. As also described above, the HLGF-1 of this invention has pre-B cell differentiating activity. Activity of this sort was demonstrated by the differentiation of pre-B cells from Ig-progenitor cells in depleted B cell and pre-B cell bone marrow cells upon the addition of various concentrations of TC-1 CM in short term liquid cultures.

This invention also relates to a purification process for isolating HLGF-1 of this invention from natural sources. This process comprises several steps. In general outline these steps were anion exchange chromatography, Con-A affinity chromatography, Sephacryl-300 gel filtration chromatography, mono-Q anion exchange and Superose 12 gel filtration chromatography.

Using the above-described process, we observed that the specific activity of the HLGF-1 of this invention increased after each purification step. We measured the number of large colonies formed in the presence of optimal levels of CSF-1 per mg of protein to measure the specific activity. However, any other assays could have as well been used.

The HLGF-1 purified in the above process may of course be used directly in the immunoregulatory and hemopoietic compositions and methods of this invention. However, we prefer to use such purified protein as a source of amino acid sequence data to permit our design of DNA probes for use in isolating and selecting a DNA sequence coding for HLGF-1 of this invention. Such DNA sequences, recombinant DNA molecules including them, and unicellular hosts transformed with them may be employed to produce large amounts of the HLGF-1 of this invention, substantially free from other proteins, for use in the compositions and therapies of this invention. More specifically, we determine the amino acid sequences of various portions and fragments of our purified HLGF-1. We then use those sequences and the degenerate DNA sequences coding for them to design a series of DNA probes potentially useful in first screening murine libraries for DNA sequences coding for the HLGF-1's of this invention, and secondly, screening a human library with a fragment of the murine HLGF-1 cDNA sequence. Such libraries include chromosomal gene banks and cDNA or DNA libraries prepared from tissue or cell lines that are demonstrated to produce the HLGF-1's of this invention. The basis for this approach is that we postulate that mouse HLGF-1 cDNA might cross hybridize to human HLGF-1 cDNA to an extent sufficient to allow selection of a human HLGF-related cDNA from our libraries.

It should be understood that a variety of cloning and selection techniques might theoretically be useful in locating and identifying DNA sequences that encode our HLGF-1s [See, e.g., T. Maniatis et al., "Molecular Cloning—A Laboratory Manual", Cold Spring Harbor (1982)]. These selected DNA sequences are then used themselves as probes to select other DNA sequences coding for HLGF and in appropriate recombinant DNA molecules to transform appropriate eukaryotic and prokaryotic hosts for the production of HLGF-1 encoded by them.

The DNA sequences and DNA molecules of the prsent invention may be expressed using a wide variety of host/vector combinations. For example, useful vectors may consist of segments of chromosomal, nonchromosomal and synthetic DNA sequences, such as various known derivatives of SV40 and known bacterial plasmids, e.g., plasmids from $E.$ $coli$ including colE1, pCR1, pBR322, pMB9 and RP4, phage DNAs, e.g., the numerous derivative of phage, e.g., NM 989, and other DNA phages, e.g., M13 and other Filamentous single-stranded DNA phages, vectors useful in yeasts, such as the $2\mu$ plasmid, vectors useful in eukaryotic cells, such as vectors useful in animal cells, such as those containing SV-40 adenovirus and retrovirus derived DNA sequences and vectors derived from combinations of plasmids and phage DNAs, such as plasmids which have been modified to employ phage DNA or other derivatives thereof.

Such expression vectors are also characterized by at least one expression control sequence that may be operatively linked to the HLGF-1 DNA sequence inserted in the vector in order to control and to regulate the expression of that cloned DNA sequence. Examples of useful expression control sequences are the lac system, the trp system, the tac system, the trc system, major operator and promoter regions of phage $\lambda$, the control region of fd coat protein, the glycolytic promoters of yeast, e.g., the promoter for 3-phosphoglycerate kinase, the promoters of yeast acid phosphatase, e.g., Pho5, the promoters of the yeast $\alpha$-mating factors, and promoters derived from polyoma, adenovirus, retrovirus, and simian virus, e.g., the early and late promoters or SV40,and other sequences known to control the expression of genes of prokaryotic or eukaryotic cells and their viruses or combinations thereof.

Among such useful expression vectors are vectors that enable the expression of the cloned HLGF-1-related DNA sequences in eukaryotic hosts, such as animal and human cells [e.g., P. J. Southern and P. Berg, *J. Mol. Appl. Genet.,* 1, pp. 327–41 (1982); S. Subramani et al., *Mol Cell. Biol.,* 1, pp. 854–64 (1981); R. J. Kaufmann and P. A. Sharp, "Amplification And Expression Of Sequences Cotransfected with A Modular Dihydrofolate Reductase Complementary DNA Gene", *J. Mol. Biol.,* 159, pp. 601–21 (1982); R. J. Kaufmann and P. A. Sharp, *Mol. Cell. Biol.,* 159, pp. 601–64 (1982) S. I. Scahill et al., "Expression And Characterization Of The Product Of A Human Immune Interferon DNA Gene In Chinese Hamster Ovary Cells", *Proc. Natl. Acad. Sci. U.S.A.,* 80, pp. 4654–59 (1983); G. Urlaub and L. A. Chasin, *Proc. Natl. Acad. Sci. U.S.A.,* 77, pp. 4216–20 (1980)].

Furthermore, within each specific expression vector, various sites may be selected for insertion of the HLGF-1-related DNA sequences of this invention. These sites are usually designated by the restriction endonuclease which cuts them. They are well recognized by those of skill in the art. It is, of course to be understood that an expression vector useful in this invention need not have a restriction endonuclease site for insertion of the chosen DNA fragment. Instead, the vector could be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, size of the protein to expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Useful expression hosts may include well known eukaryotic and prokaryotic hosts, such as strains of *E.coli*, such as *E.coli* SG-936, *E.coli* HB 101, *E.coli* W3110, *E.coli* X1776, *E.coli* X2282, *E.coli* DHI, and *E.coli* MRCl, Pseudomonas, Bacillus, such as *Bacillus subtilis*, *Streptomyces*, yeasts and other fungi, animal, such as COS cells and CHO cells, and human cells and plant cells in tissue culture.

Of course, not all host/expression vector combinations function with equal efficiency in expressing the DNA sequences of this invention or in producing the HLGF-1-like polypeptides of this invention. However, a particular selection of a host/-expression vector combination may be made by those of skill in the art after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary postexpression modifications of the desired protein.

The HLGF-1's produced by fermentation of the prokaryotic and eukaryotic hosts transformed with the DNA sequences of this invention, can then be employed in the compositions and methods of this invention.

Administration of the polypeptides, or perhaps peptides derived or synthesized from them or using their amino acid sequences, or their salts or pharmaceutically acceptable derivatives thereof, may be via any of the conventionally accepted modes of administration of hemopoietic agents or agents which exhibit immunoregulatoy activity. These include oral, parenteral, subcutaneous, intravenous, intralesional or topical administration. Local, intralesional or intravenous injection is preferred.

The compositions used in these therapies may also be in a variety of forms. These include, for example, solid, semi-solid and liquid dosage forms, such as tablets, pills, powders, liquid solutions or suspension, suppositories, injectable and infusable solutions. The preferred form depends on the intended mode of administration and therapeutic application. The compositions also will preferably include conventional pharmaceutically acceptable carriers and may include other medicinal agents, carriers, adjuvants, excipients, etc., e.g., human serum albumin or plasma preparations. Preferably, the compositions of the invention are in the form of a unit dose and will usually be administered one or more times a day.

In order that our invention herein described may be more fully understood, the following examples are set forth. It should be understood that these examples are for illustrative purposes only and should not be construed as limiting this invention in any way to the specific embodiments recited therein.

Example 1: Purification of HLGF-1 a) Anion Exchange

A zeta prep cartridge (800:LKB) was equilibrated in a 0.01M Tris/HCl Buffer, pH 7.5 containing 0.15M NaCl and 0.1% polyethylene glycol 300 (PEG). After adjusting the pH to 7.5 we pumped 10 liters batches of TC-1 CM through the zeta prep cartridge at 100 ml/min and washed with 500 ml of equilibration buffer. Bound material was sequentially eluted stepwise by the addition of NaCl to the buffer, first at 0.3M and then at 1.0M concentration. We next measured the specific activity as the number of large colonies formed in the presence of optimal levels of CSF-1 per mg of protein in a double layer agar culture system [P. Quesenberry et al., "Effect Of Endotoxin On Granulopoiesis And The In Vitro Colony-Forming Cell", Blood, 41, p. 391 (1973), modified with McCoy's media being supplemented with 0.8% minimal essential medium (MEM) essential amino acids, 0.4% MEM nonessential amino acids, 2 mmol/L of L-glutamine, 16 $\mu$g/mL of L-asparagine, 8 ug/mL of L-serine, 1 mmol/L of sodium pyruvate, $1 \times 10^4$ mol/L of 2-mercaptoethanol, and 15% pretested FCS. The specific activity of the DEAE zeta prep fraction was 46.1 U/mg of protein, or alternately utilizing a low 02 alpha media agar culture system.

b) Con-A Sepharose Chromatography

We pooled the active material from step 1 and diafiltered it against 0.02M Tris/HCl, pH 7.4 containing 0.5M NaCl and 0.1% PEG using a Millipore Pellicon concentration system with a membrane of 10,000 MW cut off. After concentrating the material to a final volume of 500 ml, we loaded it onto a Con-A Sepharose (Pharmacia, Piscataway, N.J.) column, 2.6×30 cm, previously equilibrated in the same buffer. We washed the column with 500 ml of buffer until nonbound proteins were eluted. We collected bound protein in a final volume of 500 mls by eluting with 0.25M $\alpha$-methyl mannoside. The active fraction had a specific activity of 106.8 U/mg of protein as determined by the assay in (a).

c) Sephacryl S-300 Gel Filtration Chromatography

We diafiltered the active pool against 0.01M Tris/HCl, pH 8.0 containing 0.15M NaCl and 0.1% PEG and concentrated it to a final volume of 5 ml using an Amicon ultrafiltration unit with a 10,000 MW cut off membrane. This material was then loaded onto a Sephacryl S-300 column (Pharmacia, Piscataway, N.J.), 26×87 cm, which had been previously equilibrated into the above buffer. Fractions of 6 ml were collected, pools of fractions were made for assay and each pool was concentrated on an Amicon 10,000 MW cut off membrane to a final volume of 50 mls. The specific activity of this fraction measured 1811.6 U/mg of protein as determined by the assay in (a).

d) Anion Exchange

We next loaded the active pool onto a mono Q HR16/10 column (Pharmacia, Piscataway, N.J.) previously equilibrated in 0.01M Tris/HCl, pH 8.0, buffer containing 0.15M plus 0.1% PEG. Using 50 ml of equilibration buffer, we washed the unbound material. A salt gradient was then run from 0.15M to 1.0M NaCl at 10 ml/min. and 10 ml fractions collected. We further passed 50 ml of buffer containing 1.0M NaCl to ensure maximum elution of bound proteins. We made pools of fractions and each pool was diafiltered against normal saline X 0.1% PEG and concentrated to a final volume of 10 ml using an Amicon 10,000 MW cut off membrane. The resulting specific activity was 4348 U/mg of protein as determined by the assay in (a).

e) Gel Filtration On A Superose 12 Column

We concentrated the active pool from above to 400 ul and loaded in 100 ul samples onto an FPLC Superose 12 HRS/16 column previously equilibrated in 0.01M Tris/HCl, pH 8.0, containing 0.15M NaCl plus 0.1% PEG. Each 100 ul sample was run separately and fractions were then combined. Buffer was run at 0.5 ml/min. and 1 ml fractions were finally collected. We measured a specific activity of 20,000 U/mg of protein as determined by the assay in (a).

Example 2: Synergistic Activity of HLGF-1 with CSF-1

To determine the synergistic activity of HLGF-1 we separated TC-1 CM by DE-52 cellulose (Whatman, Clifton, N.J.) that was equilibrated in 0.02 mol/L of Tris-HCl, pH 7.4, followed by G100 Sephadex (Superfine, Pharmacia, Piscataway, N.J.) chromatography. We next collected active fractions determined as >1 mm macrophage colonies per milliliter with a double agar assay [P. Quensenberry et al., infra], using ICR mouse (Dominion Labs, Dublin, Va.) bone marrow pooled and passed them over an affinity CSF-1 antibody column. Antiserum to CSF-1 was produced in male New Zealand white rabbits [R. Shadduck et al., *Blood Cells* 5, p. 421 (1979)]. We tested the unbound material at various concentrations for its ability to synergize colony formation by stage 1 CSF-1 derived from L cell CM [A. Waheed et al., "Purification of Colony-Stimulating Factor by Affinity Chromatography", *Blood* 60, p. 238 (1982)] in the double layer agar assay. CSF-1 was added to 3% agar-McCoy's underlayer in the double layer agar culture in which McCoy's media was supplemented with 0.8% minimal essential medium (MEM) essential amino acids, 0.4% MEM nonessential amino acids, 2 mmol/L of L-glutamine, 16 ug/mL of L-asparagine, 8 ug/mL of L-serine, 1 mmol/L of sodium pyruvate, $1 \times 10^4$ mol/L of 2-mercaptoethanol, and 15% pretested FCS. Also in the culture were marrow cells from BDF (Jackson Labs, Bar Harbor, Me.) mice that were plated at $5 \times 10^4$ cells/mL and the unbound G100 TC-1 CM pool at various concentrations. We counted the giant macrophage colonies 0.5 mm in diameter $5 \times 10^4$ cells as an assay. FIG. 1 depicts an increase in synergistic activity with CSF-1 by greater concentrations of the G-100 unbound pool.

Example 3: Synergistic Activity of HLGF-1 with IL3

We observed that HLGF-1 synergized with IL3 to produce giant mixed granulocyte-macrophages (GM) and GM-megakaryocyte colonies and to enhance megakaryocyte colony formation. Because CSF-1 acts synergistically with IL3 to give rise to giant macrophage colonies, we depleted TC-1 CM of CSF-1 by affinity CSF-1 antibody column chromatography. Antiserum to CSF-1 was produced in Male New Zealand white rabbits [Shadduck et al., infra] and covalently bound to cyanogen bromide activated Sepharose 4B. Specifically, we passed over the Sepharose column after dialysis against 0.05 mol/L of Tris, 0.15 mol/L of NaCl and 0.3% polyethylene glycol (PEG) buffers, pH 7.5, three pools of TC-1 CM which were concentrated ten times. We tested the unbound portion for the presence of CSF-1 by RIA and found it was free. BDF1 (Jackson Labs, Bar Harbor, Me.) and JCR (Dominion Labs, Dublin, Va.) murine target marrow cells were placed in a soft agar culture using 3% McCoy's media as described in example 2. IL3 at varying levels ranging between 43 to 160 U/ml was added to the culture along with the unbound fraction. Table 1 compares the overall increase in colony formation as a result of HLGF-1's synergistic activity.

TABLE 1
EFFECT OF TC-1 "UNBOUND" FRACTION ON IL-3-INDUCED COLONY FORMATION

| Group | Mega | Colonies/$5 \times 10^4$ Cells | | |
|---|---|---|---|---|
| | | Total Mega | >2 mm | >1 mm |
| IL 3 | 7.5 ± 4.3 | 10 ± 4 | 3.7 ± 1.2 | 51 ± 19 |
| IL 3 + unbound fraction | 17.3 ± 4.7 | 24.3 ± 6.2 | 19 ± 9.3 | 67 ± 21 |

Mega, pure megakaryocyte colonies of more than three cells; total mega, pure and mixed mega colonies; >2 mm mixed, colonies >2 mm in diameter predominantly granulocyte-mcarophage (GM) or macrophage, but also including GM-Mega.

To assess the synergy further, we next added the unbound material at a concentration of 2% with 4.3 ng/mL of IL3 to post-fluorouracil murine BDF1 (Jackson Labs, Bar Harbor, Me.) target marrow cells ($0.5 \times 10$/mL) in a double layer agar assay [P. Quesenberry et al., infra] using McCoy's media as described in Example 2. FIG. 2 illustrates the synergistic effect of HLGF-1 on IL3 stimulated colony formation in contrast to solely IL3 or unbound material stimulated colony formation. We found the major synergistic effect is to increase colony size with no overall stimulation of total clony formation.

Example 4: Synergistic Activity Of HLGF-1 With GM-CSF

We observed a similar activity of HLGF-1 giving rise to giant granulocyte-macrophage colonies in the presence of murine lung CM (a source of GM-CSF) [P. Quesenberry et al., Blood, 45, p. 289 (1975)]). Murine BDF1 marrow cells ($0.5 \times 10^5$ cells/mL) were cultured in a double-layer agar assay [P. Quesenberry et al., infra] with 11.5% 10 x TC-1 CM plus 8.3% GM-CSF. FIG. 3 depicts the synergistic effect of HLGF-1 on GM-CSF stimulated colony formation in contrast to solely GM-CSF (8.3%) or TC-1 CM stimulated colony formation.

Example 5: Induction Of Pre-B Cell Differentiation

We obtained bone marrow cells from BDF1 mice (Jackson Laboratory, Bar Harbor, Me.) by aseptically flushing femora with ice cold RPM1 1640 medium (GIBCO, Grand Island, N.Y.) which contained 2% fetal calf serum (FCS, Hyclone, Logan, Utah). Large debris were allowed to settle out into a 1 ml underlayer of FCS for 3 minutes on ice and remaining cells transferred to a second FCS cushion and pelleted at 400 x G for 7 minutes. We next depleted from the cells B cells by incubation on plates, which were previously incubated with 50 ug of affinity purified goat antimouse Ig in 0.5M tris hydroxymethyl aminomethane buffer, pH 9.5, at room temperature for 70 min. and washed three times with phosphate buffered saline ($2.5 \times 10^6$ cells/plate, 4° C., 70 min.). Afterwards, we depleted the cells of pre-B cells by twice incubating them on plates previously coated with 14.8 monclonal antibody (ATCC, Rockville, Md.). In order to coat the plates we took the anti-mouse Ig coated plates, washed them three times, and then incubated with 100 ul 14.8 CM concentrated ten times (100 ug antibody) in 3 mls PBS at 4° C. for 30 min. We next purified TC-1 CM by ammonium sulfate precipitation, DE-52 batch elution, G-100 gel filtration, CSF-1 affinity chromatography and Con-A affinity chromatography [K. S. Landreth et al., "Regulation Of Human B Lymphopoiesis: Effect Of Urinary Activity Associated With Cyclic Neutropenia", *J. Immunol*, 134, p. 2305 (1985)].

The depleted bone marrow cells were cultured at (sIg-, 14.8- cells) at $1\times10^4$/ml in RPMl 1640 medium containing 5% FCS, essential and nonessential amino acids, 200 mM L-glutamine, vitamin (Gibeo, Grand Island, N.Y.) $5\times10^{-5}$ M 2ME, and penicillin and streptomycin, we added the TC-1 CM at concentration of 5% to 10%.

Cultures were harvested at 18 or 42 hours by vigorous pipetting. We assayed immunoglobulin heavy and light chain expression and binding on 14.8 monoclonal antibody by immunofluorescence. FIG. 4 depicts increased levels of pre-B cell production, presented as absolute number of pre-B cells or 14.8 +cells generated per $10^6$ cells cultured, when compared to cultures containing 10 x concentrated media and fetal calf serum controls.

In order to demonstrate that CSF-1 is not responsible for pre-B cell differentiation, we further freed TC-1 CM of CSF-1 by running it over an anti-CSF-1 affinity column. Afterwards CSF-1 was undetectable by RIA. We found pre-B cell generating activity was still retained.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A substantially pure HLGF-1 obtained from crude HLGF-1, the pure HLGF-1 being characterized by a synergistic activity with CSF-1, IL-3 and GM-CSF and a potentiating activity of pre-B cell differentiation, wherein the HLGF-1 has a molecular weight of approximately 110,000 to 140,000 daltons on SDS PAGE, and wherein the crude HLGF-1 is isolated from bone marrow cells.

2. A method for purifying crude HLGF-1 comprising subjecting crude HLGF-1 to:
   (a) anion exchange chromatography on a DEAE zeta prep;
   (b) Con-A affinity chromatography;
   (c) Sephacryl S-300 gel filtration chromatography;
   (d) mono-Q anion exchange on a mono-Q column; and
   (e) Superose 12 column gel filtration chromatography.

3. A pharmaceutical composition comprising a therapeutically effective amount of HLGF-1 according to claim 1 in a pharmaceutically acceptable vehicle.

4. Polypeptide according to claim 1 wherein the HLGF-1 is human HLGF-1.

5. A pharmaceutical composition comprising an effective amount of the polypeptide according to claim 4 and a pharmaceutically acceptable carrier.

* * * * *